United States Patent
Didomenico et al.

(10) Patent No.: US 6,723,989 B1
(45) Date of Patent: Apr. 20, 2004

(54) REMOTE EMISSIONS SENSING SYSTEM AND METHOD WITH A COMPOSITE BEAM OF IR AND UV RADIATION THAT IS NOT SPLIT FOR DETECTION

(75) Inventors: John Didomenico, Tucson, AZ (US); Craig S. Rendahl, Tucson, AZ (US)

(73) Assignee: Envirotest Systems Corporation, East Granby, CT (US)

( * ) Notice: Subject to any disclaimer, the term of this patent is extended or adjusted under 35 U.S.C. 154(b) by 492 days.

(21) Appl. No.: 09/704,565

(22) Filed: Nov. 3, 2000

(Under 37 CFR 1.47)

Related U.S. Application Data

(63) Continuation of application No. 09/520,165, filed on Mar. 7, 2000, now abandoned, which is a continuation of application No. 09/398,198, filed on Sep. 17, 1999, now abandoned.
(60) Provisional application No. 60/100,731, filed on Sep. 17, 1998.

(51) Int. Cl.[7] .............................................. G01N 21/00
(52) U.S. Cl. .............................. 250/339.05; 250/338.5; 250/339.11
(58) Field of Search ......................... 250/339.05, 338.5, 250/339.11, 339.13

(56) References Cited

U.S. PATENT DOCUMENTS

| | | |
|---|---|---|
| 2,930,893 A | 3/1960 | Lane et al. |
| 3,143,648 A | 8/1964 | Bradley et al. |
| 3,171,027 A | 2/1965 | Wallack |
| 3,517,190 A | 6/1970 | Astheimer |
| 3,593,023 A | 7/1971 | Dodson et al. |
| 3,630,072 A | 12/1971 | Traver |
| 3,696,247 A | 10/1972 | McIntosh et al. |
| 3,743,426 A | 7/1973 | Steinberg |
| 3,761,715 A | 9/1973 | Menzies |
| 3,761,724 A | 9/1973 | Dennis |
| 3,766,380 A | 10/1973 | Menzies |
| 3,841,763 A | 10/1974 | Lewis |
| 3,849,005 A | 11/1974 | Girard et al. |
| 3,891,848 A | 6/1975 | Fletcher et al. |
| 3,908,167 A | 9/1975 | Hadden et al. |
| 3,931,462 A | 1/1976 | Exton |
| 3,957,372 A | 5/1976 | Cross et al. |
| 3,958,122 A | 5/1976 | Cross et al. |
| 3,973,848 A | 8/1976 | Jowett et al. |

(List continued on next page.)

OTHER PUBLICATIONS

Guenther, Paul L., et al., "A Hydrocarbon Detector for the Remote Sensing of Vehicle Exhaust Emissions", *Review of Scientific Instruments*, vol. 56, No. 4, Apr. 1995, pp. 3024–3029.

(List continued on next page.)

*Primary Examiner*—Constantine Hannaher
*Assistant Examiner*—Otilia Gabor
(74) *Attorney, Agent, or Firm*—Mintz Levin Cohn Ferris Glovsky and Popeo PC

(57) ABSTRACT

A system and method for remote emissions detection that uses a composite beam of ultraviolet (UV) and infrared (IR) radiation. The composite beam is used to perform spectroscopic measurements on an emissions source plume. The composite beam is not split during detection, and may, among other things, be used to detect $NO_x$ in the emissions plume.

7 Claims, 2 Drawing Sheets

U.S. PATENT DOCUMENTS

| | | |
|---|---|---|
| 3,976,884 A | 8/1976 | Acton et al. |
| 4,135,092 A | 1/1979 | Milly |
| 4,160,373 A | 7/1979 | Cross et al. |
| 4,204,121 A | 5/1980 | Milly |
| 4,204,768 A | 5/1980 | N'Guyen |
| 4,323,777 A | 4/1982 | Baskins |
| 4,390,785 A | 6/1983 | Faulhaber et al. |
| 4,420,687 A | 12/1983 | Martinez et al. |
| 4,426,640 A | 1/1984 | Becconsall et al. |
| 4,477,190 A | 10/1984 | Liston et al. |
| 4,480,191 A | 10/1984 | Karpowycz |
| 4,489,239 A | 12/1984 | Grant et al. |
| 4,490,043 A | 12/1984 | Cramp |
| 4,490,613 A | 12/1984 | Brame |
| 4,492,862 A | 1/1985 | Grynberg et al. |
| 4,496,839 A | 1/1985 | Berstein et al. |
| 4,516,858 A | 5/1985 | Gelbwachs |
| 4,544,273 A | 10/1985 | Berndt |
| 4,553,032 A | 11/1985 | Borken et al. |
| 4,560,873 A | 12/1985 | McGowan et al. |
| 4,663,961 A | 5/1987 | Nelson et al. |
| 4,707,603 A | 11/1987 | Jaatinen et al. |
| 4,710,630 A | 12/1987 | Kuppenheimer et al. |
| 4,719,360 A | 1/1988 | Kontani et al. |
| 4,746,218 A | 5/1988 | Lord |
| 4,765,961 A | 8/1988 | Schiff et al. |
| 4,771,176 A | 9/1988 | Schiefer et al. |
| 4,795,253 A | 1/1989 | Sandridge et al. |
| 4,798,464 A | 1/1989 | Boostrom |
| 4,810,884 A | 3/1989 | Carlson |
| 4,818,705 A | 4/1989 | Schneider et al. |
| 4,829,183 A | 5/1989 | McClatchie et al. |
| 4,875,084 A | 10/1989 | Tohyama |
| 4,902,889 A | 2/1990 | Sodi |
| 4,924,095 A | 5/1990 | Swanson, Jr. |
| 4,990,780 A | 2/1991 | Lee et al. |
| 4,999,498 A | 3/1991 | Hunt et al. |
| 5,041,723 A | 8/1991 | Ishida et al. |
| 5,055,685 A | 10/1991 | Sugimoto |
| 5,055,697 A | 10/1991 | Manoogian et al. |
| 5,060,505 A | 10/1991 | Tury et al. |
| 5,099,680 A | 3/1992 | Fournier et al. |
| 5,105,651 A | 4/1992 | Gutmann |
| 5,129,257 A | 7/1992 | Carduner et al. |
| 5,157,258 A | 10/1992 | Gunning, III et al. |
| 5,184,017 A | 2/1993 | Tury et al. |
| 5,189,677 A | 2/1993 | Yry |
| 5,210,702 A | 5/1993 | Bishop et al. |
| 5,210,765 A | 5/1993 | Flint et al. |
| 5,246,868 A | 9/1993 | Busch et al. |
| 5,252,828 A | 10/1993 | Kert et al. |
| 5,294,796 A | 3/1994 | Fee |
| 5,306,913 A | 4/1994 | Noack et al. |
| 5,319,199 A | 6/1994 | Stedman et al. |
| 5,325,380 A | 6/1994 | Clendening et al. |
| 5,325,393 A | 6/1994 | Nighan et al. |
| 5,327,356 A | 7/1994 | Lang et al. |
| 5,332,901 A | 7/1994 | Eckles et al. |
| 5,343,043 A | 8/1994 | Johnson |
| 5,371,367 A | 12/1994 | DiDomenico et al. |
| 5,373,160 A | 12/1994 | Taylor |
| 5,386,373 A | 1/1995 | Keeler et al. |
| 5,401,967 A | 3/1995 | Stedman et al. |
| 5,418,366 A | 5/1995 | Rubin et al. |
| 5,424,543 A | 6/1995 | Dombrowski et al. |
| 5,451,787 A | 9/1995 | Taylor |
| 5,489,777 A * | 2/1996 | Stedman et al. ......... 250/338.5 |
| 5,498,872 A | 3/1996 | Stedman et al. ......... 250/338.5 |
| 5,563,420 A | 10/1996 | Sullivan et al. ......... 250/504 R |
| 5,572,424 A | 11/1996 | Kellogg et al. |
| 5,583,765 A | 12/1996 | Kleehammer |
| 5,589,629 A | 12/1996 | Quinn |
| 5,591,975 A | 1/1997 | Jack et al. ............... 250/338.5 |
| 5,621,166 A | 4/1997 | Butler |
| 5,644,133 A | 7/1997 | Didomenico et al. |
| 5,693,872 A | 12/1997 | Quinn |
| 5,719,396 A | 2/1998 | Jack et al. |
| 5,726,450 A | 3/1998 | Peterson et al. |
| 5,731,510 A | 3/1998 | Jones et al. |
| 5,753,185 A | 5/1998 | Mathews et al. |
| 5,831,267 A | 11/1998 | Jack et al. |
| 6,307,201 B1 * | 10/2001 | DiDomenico et al. . 250/339.13 |

OTHER PUBLICATIONS

"Proposal/Quote for Unstaffed On–Road Emissions Measurement Systems, Services" in response to Phase IV—RFQ #94/95–003, prepared by Remote Solving Technologies, Inc. delivered to Department of Consumer Affairs, Bureau of Automotive Repair, Sacramento, California, Sep. 1, 1995.

Steven H. Cadle, "Measurement of Exhaust Particulate Matter Emissions from in–Use Light–Duty Motor Vehicles in the Denver, Colorado Area," Final Report, prepared for Coordinating Research Council, Atlanta, Georgia, Dec. 9, 1997, prepared by General Motors R&D Center, Michigan; 20 pages.

Steven H. Cadle, "Measurement of Exhaust Particulate Matter Emissions from in–Use Light–Duty Motor Vehicles in the Denver, Colorado Area," Final Report, prepared for Coordinating Research Council, Atlanta, Georgia, Mar. 24, 1998, "Appendix E. University of Denver Remote Sensing Observation of Smoking Vehicles," prepared by General Motors R&D Center, Michigan; 20 pages.

Robert D. Stephens, et al., "Remote Sensing of Carbon Monoxide Emissions from On–Road Vehicles," Environmental Science Department, General Motors Research Laboratories, Michigan for presentation to Air and Waste Management Association, NC, May 1, 1990, 48 pages.

"Description and Documentation for Interim Vehicle Clean Screening Credit Utility," Draft Report, United States Environmental Protection Agency, May 1998, 40 pages.

David S. E. Petherick, "Ontario's Indoor, Controlled–Mode Remote Sensing I/M Prescreen Concept," Ministry of Transportation of Ontario, Copyright 1996 Society of Automotive Engineers, Inc., 9 pages.

P. A. Walsh, et al., "Texas 1996 Remote Sensing Feasibility Study," Final Report, prepared for Texas Natural Resource Conservation Commission, Austin, Texas, Aug. 29, 1997, prepared by Desert Research Institute, Energy and Environmental Engineering Center, Reno, Nevada, 9 pages.

"On Road Emissions Measurement System—Specifications," Bureau of Automotive Repair, Aug. 30, 1999, Revision—J, 15 pages.

Craig, S. Rendahi, "Further Analysis of Wisconsin's Remote Vehicle Emissions Sensing Feasibility Studies" "Quality Control Efforts of Remote Vehicle Emissions Sensing," and "Data Handling and Validation from Wisconsin's Remote Vehicle Emissions Sensing Studies," Presented at the Air & Waste Management Annual Measurement of Toxics and Related Pollutants Conference, Research Triangle Park, North Carolina, 5/96, 34 pages.

James D. Peterson, et al., "Find and Fix the Polluters", Chemtech, Jan. 1992, Copyright 1992 American Chemical Society, 7 pages.

RSD 1000 Operator's Manual (Preliminary), Remote Sensing Technologies, IFB No. 94019, Jun. 1993, 66 pages.

RSD–1000 Remote Sensing Device Information Package to Mr. Wolf Klassen, Department of Natural Resources, Presented by Dennis L. Smith, Feb. 24, 1993, 123 pages.

Robert D. Stephens, et al., "An Experimental Evaluation of Remote Sensing–Based Hydrocarbon Measurement: A Comparison to FID Measurements", *Journal of the Air & Waste Management Association*, vol. 46, Feb. 1996, pp. 148–158.

Donald H. Stedman, "Automobile Carbon Monoxide Emission", *Environmental Science & Technology*, vol. 23, No. 2, 1989, pp. 147–149.

Masayuki Adachi, et al., "Automotive Emission Analyses Using FTIR Spectophotometer", Published by the Society of Automotive Engineers, SAE#920723, pp. 820–827.

Michael D. Koplow, et al., "Characterization of On–Road Vehicle NO Emissions by Means of a TILDAS Remote Sensing Instrument", Published by the Coordinating Research Council, Published for the $7^{th}$ CRC On–Road Vehicle Emissions Workshop, Mar. 11, 1997, pp. 1–25.

Scott E. McClaren, et al., "Comparison of an Open Path UV and FTIR Spectrophotometer", Published by the Air & Waste Management Association, published for Presentation at the $85^{th}$ Annual Meeting & Exhibition, Kansas City, Missouri, Jun. 21–26, 1992, pp. 1–10.

"Developing an Inspection/Maintenance Program for Alternatively–Fueled Vehicles", Third Interim Report Submitted to the California Bureau of Automotive Repair, Submitted by Radian Corporation, Apr. 20, 1983, 147 pages.

Iain Frederick McVey, "Development of a Remote Sensor for Mobile Source Nitric Oxide", A Thesis Presented to the Faculty of Natural Sciences, Mathematics, and Engineering, University of Denver. Nov. 1992, 111 pages.

S. P. Beaton, et al., "Emission Characteristics of Mexico City Vehicles", *Journal of the Air & Waste Management Association*, vol. 42, No. 11, Nov. 1992, pp. 1424–1429.

Douglas R. Lawson, et al., "Emissions from In–Use Motor Vehicles in Los Angeles: A Pilot Study of Remote Sensing and the Inspection and Maintenance Program", *Journal of the Air & Waste Management Association*, vol. 40, No. 8, Aug. 1990, pp. 1096–1105.

Yi Zhang, et al., "Enhancement of Remote Sensing for Mobile Source Mitric Oxide", *Journal of the Air & Waste Management Association*, vol. 46, Jan. 1996, pp. 25–29.

Donald H. Stedman, et al., "Evaluation of a Remote Sensor for Mobile Source CO Emissions", U.S. Environmental Protection Agency, CR–815778–01–0, Report No. EPA/600/4–90/032, Jan. 1991, 90 pages.

James Butler, et al., "Factors Affecting the NDIR Measurement of Exhaust Hydrocarbons", Published by the Coordinating Research Council, Published for the CRC $5^{th}$ On–Road Vehicle Emissions Workshop, 1995, 16 pages.

Scott E. McLaren, et al., "Flux Measurements Using Simultaneous Long Path Ultraviolet and Infrared Spectroscopy", Published by the Air & Waste Management Association, Published for Presentation at the $83^{rd}$ Annual Meeting & Exhibition, Pittsburgh, Pennsylvania, Jun. 24–20, 1990, 7 pages.

Gary A. Bishop, et al., "Infrared Emission and Remote Sensing", *Journal of the Air & Waste Management Association*, vol. 42, No. 5, May 1992, pp. 695–697.

Hakan Axelsson, et al., "Measurement of Aromatic Hydrocarbons with the DOAS Technique", *Applied Spectroscopy*, vol. 49, No. 9, pp. 1254–1260.

Gary A. Bishop, et al., "Method Comparisons of Vehicle Emissions Measurements in the Fort McHenry and Tuscarora Mountain Tunnels", *Atmospheric Environment*, vol. 30, No. 12, 1996, pp. 2307–2316.

Donald H. Stedman, et al., "NOx Data by Remote Sensing", Published by the Coordinating Research Council, Published for the $5^{th}$ CRC On–Road Vehicle Emissions Workshop, Apr. 3–5, 1995, 16 pages.

Donald H. Stedman et al., "On–Road Carbon Monoxide and Hydrocarbon Remote Sensing in the Chicago Area", Final Report Prepared by University of Denver Chemistry Department, Prepared for Illinois Department Energy and Natural Resources, Office of Research and Planning, Illinois Contract AQ 40, Project 91/122, Report No. ILENR/RE–AQ–91.14, Oct. 1991, pp. 1–70.

Gary A. Bishop, et al., "On–Road Carbon Monoxide Emission Measurement Comparisons for the 1988–1969 Colorado Oxy–Fuels Program", *Environmental Science & Technology*, vol. 24, No. 6, 1990, pp. 843–847.

Donald H. Stedman, et al., "On–Road CO Remote Sensing in the Los Angeles Basin", Final Report Prepared for the Research Division, California Air Resources Board, Submitted by University of Denver Chemistry Department, Aug. 1991, Contract No. A932–189, 70 pages.

Scott McLaren, "Open Path Spectrometers for Atmospheric Monitoring", A Dissertation Presented to the Faculty of Natural Sciences, Mathematics and Engineering, Nov. 1995, 170 pages.

Carole E. Lyons, et al., "Remote Sensing Enhanced Motor Vehicle Emissions Control for Pollution Reduction in the Chicago Metropolitan Area: Sitting and Issue Analysis", Final Report Prepared by University of Denver Atmospheric Science Center, Prepared for Illinois Department of Energy and Natural Resources, Office of Research and Planning, Illinois Contract AQ 30, Project 90/009, Report No. IL ENR/RE–AQ–91/15, Oct. 1981 pp. 1–85.

Peter John Popp, "Remote Sensing of Nitric Oxide Emissions from Planes, Trains and Automobiles", A Dissertation Presented to the Faculty of Natural Sciences, Mathematics and Engineering, Aug. 1999, 170 pages.

Brett C. Singer, et al., "Scaling of Infrared Remote Sensor Hydrocarbon Measurements for Motor Vehicle Emission Inventory Calculations", *Environmental Science & Technology*, vol. 32, No. 21, 1998, pp. 3241–3248.

Lucian W. Chaney, "The Remote Measurement of Traffic Generated Carbon Monoxide", *Journal of the Air Pollution Control Association*, vol. 33, No. 3, Mar. 1983, pp. 220–222.

Jose Luis Jimenez–Palacios, "Understanding and Quantifying Motor Vehicle Emissions with Vehicle Specific Power and TILDAS Remote Sensing", A Dissertation Presented to the Department of Mechanical Engineering, Feb. 1999, 360 pages.

"Vehicle Inspection Instrumentation", Published by the Lockheed Missils and Space co., Inc. Report No. ARB–R–643–73–26, Jun. 30, 1973, 99 pages.

John E. Sigsby, Jr., et al., "Volatile Organic Compound Emissions from 48 In–Use Passenger Cars", *Environmental Science & Technology*, vol. 21, No. 5, 1987, pp. 466–475.

Yi Zhang, et al., "Worldwide On–Road Vehicle Exhaust Emissions Study by Remote Sensing", *Environmental Science & Technology*, vol. 29, No. 9, 1995, pp. 2286–2294.

Technical Proposal—"Vehicle Inspection Instrumentation"; submitted to California Air Resources Board; Sep. 1, 1971, Lockheed Palo Alto Research Laboratory, Lockheed Missiles & Space Company—A Group Division of Lockheed Aircraft Corporation, Palo Alto, California.

Hoshizaki, et al., Final Report—"Vehicle Inspection Instrumentation"; submitted to California Air Resources Board; Jun. 1973, Lockheed Palo Alto Research Laboratory, Lockheed Missiles & Space Company—A Group Division of Lockheed Aircraft Corporation, Palo Alto, California.

http://www.epa_gov/otao/15-remot.htm; "Remote Sensing: A Supplemental Tool for Vehicle Emission Control," Aug. 1993, EPA 400-F-92-017, Fact Sheet OMS-15; 4 pages.

Paul Stockwell, "Tunable Diode Laser Systems Break New Ground in Water Vapour Analysis"; IMA Ltd., Unit Newall Hall Park, Otley, West Yorkshire, United Kingdom: [undated]; 8 pages.

Mark G. Allen, "Diode Laser Absorption Sensors for Gas Dynamic and Combustion Flows," Copyright 1998 Measurement Science and Technology 9; 81 pages.

Kerry L Swayne, Infrared Remote Sensing of On-Road Motor Vehicle Emissions in Washington State Mar., 1999, Air Quality Program, Washington State Department of Ecology, Washington; Publication #99-204; 20 pages.

Gary A. Bishop. et al., "Oxygenated Fuels, A Remote Sensing Evaluation," SAE Technical Paper Series; Copyright 1989 Society of Automotive Engineers, Inc.; 7 pages.

Robert D. Stephens, "Remote Sensing Data and a Potential Model of Vehicle Exhaust Emissions," Nov. 1994, vol. 44, Journal of Air & Waste Management Association, pp. 1264-1292.

"An Analysis of On-Road Remote Sensing as a Tool for Automobile Emissions Control," Final Report Prepared by University of Denver Chemistry Department, Colorado, Mar. 1990; 174 pages; prepared for Illinois Department of Energy and Natural Resources.

Robert D. Stephens, et al., "Remote Sensing Measurements of In-Use Vehicle Carbon Monoxide and Hydrocarbon Exhaust Emissions," Environmetnal Science Department, Michigan, to be presented to Society of Automotive Engineers Government/Industry Meeting, Washington, D.C., May 15, 1991; 9 pages.

Thomas C. Austin, et al., "An Evaluation of "Remote Sensing" for the Measurement of Vehicle Emissions," prepared for The California Air Resources Board and The California I/M Review Committee, Aug. 28, 1990, 30 pages; prepared by Sierra Research, Inc., California.

Robert D. Stephens, et al., "Remote Sensing Measurements of Carbon Monoxide Emissions from On-Road Vehicles," Copyright Jan. 1991, Air & Waste Management Association, Vol. 42, No. 1, pp. 39-48.

Donald H. Stedman, et al., "Remote Sensing of On-Road Vehicle Emissions," Final Report to Coordinating Research Council, The University of Denver, Jan. 6, 1992, 21 pages.

Peter Popp, et al., "Development of a High-Speed Ultraviolet Spectrophotometer Capable of Real-Time NO and Aromatic Hydrocarbon Detection in Vehicle Exhaust," Department of Chemistry, University of Denver, Colorado, Prepared for Proceedings of the $7^{th}$ CRC On-Road Vehicle Emissions Workshop, San Diego, California, Apr. 9-11, 1997; 10 pages.

John Didomenico, et al., "Prelimiary Results from Cold Start Sensor Testing," Presented to $7^{th}$ CRC On-Road Vehicle Emissions Workshop, San Diego, California Apr. 9-11, 1997; 1 page.

Gary A. Bishop, et al., "Enhancements of Remote Sensing for Vehicle Emissions in Tunnels," Air & Waste Management Association, vol. 44, Feb. 1994, pp. 169-175.

Paul Leonard Guenther, "Contributions to On-Road Remote Sensing of Automobile Exhaust," A Thesis Presented to the Faculty of Natural Sciences, Mathematics, and Engineering, University of Denver, Jun. 1992, 95 pages.

Donald H. Stedman, et al., "On-Road Remote Sensing of CO and HC Emissions in California," Prepared for Research Division, California Air Resources Board, Sacramento, CA, submitted by University of Denver Chemistry Department, Feb. 1994, 136 pages.

"Unstaffed On-Road Emissions Measurement Systems Services," Prepared by Parsons Engineering Science, Inc., Pasadena, California, Sep. 1995.

* cited by examiner

REMOTE EMISSIONS SENSING SYSTEM AND METHOD WITH A COMPOSITE BEAM OF IR AND UV RADIATION THAT IS NOT SPLIT FOR DETECTION

This application is a continuation of U.S. application Ser. No. 09/520,165, filed Mar. 7, 2000 now abandoned, which is a continuation of U.S. application Ser. No. 09/398,198, filed Sep. 17, 1999 now abandoned, which claims priority to U.S. Provisional Patent Application Serial No. 60/100,731 filed Sep. 17, 1998.

FIELD OF THE INVENTION

The invention relates to a remote emissions sensing system and method that uses a composite detector beam of infrared (IR) and ultraviolet (UV) radiation. The detector beam is used to perform spectroscopic measurements upon an emissions source and the beam is not split during detection.

BACKGROUND OF THE INVENTION

Remote emissions sensing systems generally are known. One such system comprises a source of electromagnetic radiation arranged to pass a beam of radiation through the exhaust plume of a motor vehicle as the motor vehicle passes by the system, and one or more detectors arranged to receive the radiation after it passes through the exhaust plume of the vehicle. Filters may be associated with one or more detectors to detect the intensity of electromagnetic radiation at a particular wavelength or range of wavelengths. The wavelengths may be selected to correspond to wavelengths absorbed by molecular species of interest in an exhaust plume (e.g., HC, CO, $CO_2$, $NO_x$, or other molecular species). The detector's output voltage represents the intensity of the electromagnetic radiation measured by that detector. The voltages are input to a processor. The processor calculates the difference between the known intensity of the electromagnetic radiation source and the intensity detected by the detectors to determine the amount of absorption by particular molecular species (based on predetermined wavelengths with that species). Based on the measured absorption(s), the concentration of one or more molecular species in the emissions may be determined in a known manner. Such systems generally take a plurality of measurements (e.g., 50) over a predetermined period of time (e.g., 0.5 seconds). These measurements are then plotted and analyzed to determine concentrations of target emissions. When using a plurality of measurements, however, if one or more measurements are inaccurate, concentration calculations may be erroneous or invalid. For various reasons, inaccuracies can occur when remotely sensing emissions.

Some remote emission sensing systems do not have the capability to detect nitrous oxides ($NO_x$). Other systems detect $NO_x$ with a UV beam and other molecular species with an IR beam. In one such system, the UV and IR beams are split into separate beams at the detector module. One reason for this splitting is that unequal detection times have been believed necessary for the UV and IR portions of the beam. For example, a longer UV detection time has been believed necessary to ensure adequate $NO_x$ detector signal. One problem with such a system is that unequal detection times require additional system elements which increase the difficulty in aligning the system. Other drawbacks exist.

SUMMARY OF THE INVENTION

One object of the invention is to overcome these and other drawbacks of existing systems.

Another object of the invention is to provide a remote emissions sensing system and method with a composite beam of IR and UV radiation that detects $NO_x$ and at least one other molecular species, where the alignment of the system is relatively easier than the alignment of a system wherein the UV and IR beams are split for detection.

Another object of the invention is to provide a remote emissions sensing system and method with a composite beam of IR and UV radiation that is not split for detection.

Another object of the invention is to provide a remote emissions sensing system and method with a composite beam of IR and UV radiation that detects $NO_x$ and at least one other molecular species, where the composite beam is alternately incident upon a $NO_x$ detector and a detector for the at least one other molecular species.

DESCRIPTION OF THE PREFERRED EMBODIMENT

Figure 1:
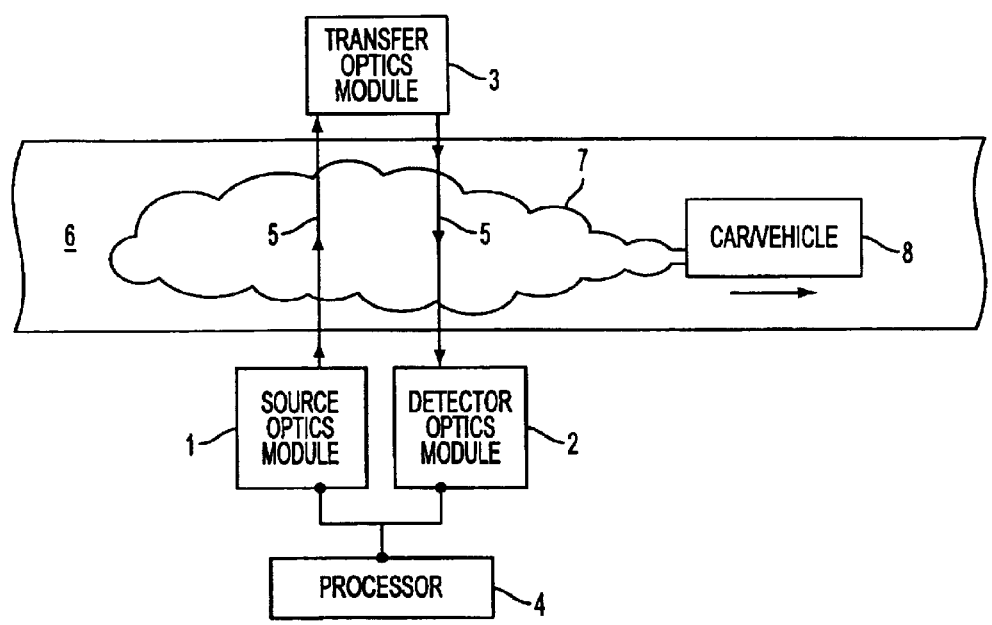
FIG. 1 is a schematic block diagram that depicts the overall remote emissions sensing system in accordance with one embodiment of the present invention.

FIG. 1 depicts one embodiment of a remote sensing exhaust emission detector system in accordance with the present invention. According to this embodiment, the exhaust emission detector system includes: source optics module 1, detector optics module 2, transfer optics module 3, and processor 4. According to one embodiment of the invention, the processor 4 is operatively connected both source optics module 1 and detector optics module 2.

Source optics module 1 may include one or more sources of electromagnetic radiation which generates and emits a radiation beam 5 which may be collimated. According to one embodiment of the invention, the beam 5 emitted at source optics module 1 may include at least infrared (IR) and ultraviolet (UV) radiation. Other beam types are possible.

As shown in FIG. 1, beam 5 may be directed across a roadway 6 along a predetermined path where it may impinge upon transfer optics module 3 located opposite to source optics module 1. Transfer module 3 directs beam 5 back across roadway 6 to detector optics module 2. Other system configurations may be used. For example, according to one embodiment of the invention, transfer optics module 3 is not used at all. Instead, the source 1 and detector optics 2 may be disposed on opposite sides of the roadway such that detector optics module 2 receives beam 5 directly from source optics module 1. In any case, beam 5 is aligned to traverse a predetermined path that intersects at least a portion of an emissions source. In some embodiments, the emissions source may comprise an exhaust plume emitted from a car or other motor vehicle 8 that travels on roadway 6. When vehicle 8 passes along roadway 6, beam 5 may be aligned to pass through the exhaust plume 7 of the vehicle.

Figure 2:
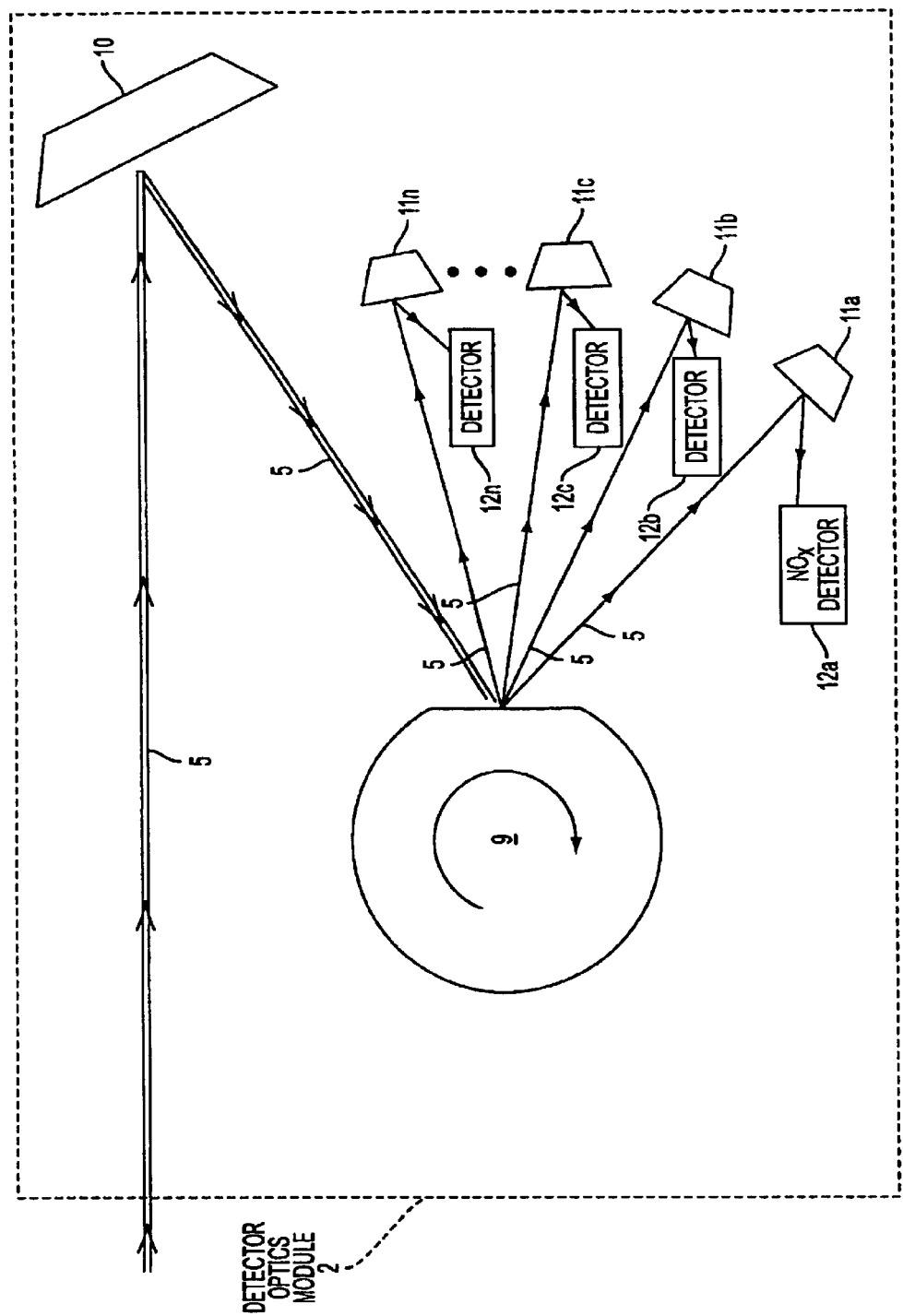
FIG. 2 is a schematic diagram of the detector optics module used in the remote sensing system according to one embodiment of the invention.

FIG. 2 is an illumination of one embodiment of detector optics module 2. The detector optics module 2 may be used to guide beam 5 to appropriate detectors. Beam 5 may be guided by any suitable configuration of beam guides. For example, lenses, mirrors, fiber optics and other elements may be used to guide beam 5. According to one embodiment of the invention, the incoming beam 5 may initially be directed onto a primary focusing mirror 10, as shown in FIG.

2. The primary focusing mirror 10 may be pivotally and rotatably mounted on a support that is attached to the base (not shown) of the detector optics module 2. Further, the primary focusing mirror 10 may, for example, be pivoted at an angle such that the mirror 10 reflects the incoming beam 5 onto the mirrored surface 13 of a rotating mirror assembly 9. Other configurations of detector optics module 2 are also possible. For example, primary focusing mirror 10 may be eliminated if beam 5 is configured to be directly incident upon appropriate detectors. Alternatively, additional focusing mirrors and optics (e.g., lenses, fiber optics, etc.) may be used in conjunction with primary focusing mirror 10.

Detector optics module 2 may also include additional elements to guide beam 5. For example, a rotating mirror 9 may be used. Rotating mirror assembly 9 may be located on top of a mount assembly (not shown) which may contain a drive motor to cause mirror assembly 9 to rotate. Such a mount assembly may be attached to the base of detector optics module. Although only one mirror is shown in FIG. 2, rotating mirror assembly 9 may also take the form of a multi-faceted structure, such as a dodecagon, where one or more sides of the structure may have a reflective surface.

As stated above, detector optics module 2 may be employed to guide beam 5 to appropriate detectors. Detector optics module 2 guides beam 5 in such a manner that beam 5 is not split during detection. Not splitting beam 5, among other things, simplifies the alignment of the system components. In one embodiment, beam 5 is guided, without splitting, by using guide elements that sequentially direct beam 5 to predetermined detector locations. For example, a rotating mirror 9 may be employed to guide beam 5 without splitting. As shown in FIG. 2, rotating mirror assembly 9 spins such that when beam 5 is incident upon the mirrored surface of the rotating mirror assembly 9, the beam 5 is reflected from the rotating mirror assembly 9 onto one or more secondary, focusing mirrors 11a–11n, in a sequential manner. According to one embodiment of the invention, one or more of these secondary mirrors may be horizontally aligned with rotating mirror assembly 9 such that the secondary mirrors 11a–11n reflect and focus the beam 5 onto one or more detectors 12a–12n. Alternatively, other optical systems may be used to spatially separate the incident beam 5 for delivery to the various detectors 12a–12n. For example, lenses, mirrors, optical fibers, etc., may be used to deliver the incident beam 5 to detectors 12a–12n.

At least one of detectors 12a–12n is capable of detecting and measuring nitrous oxides ($NO_x$) without requiring beam 5 to be split. Preferably, the particular $NO_x$ detector used is capable of adequately detecting $NO_x$ concentrations (in a known manner) even when it is one of n detectors that are sequentially irradiated by beam 5 via rotating mirror 9. One example of a detector that is suitable for use in this embodiment is a real time photospectrometer. In one embodiment, a fiber optic light tube may be positioned at 12a and used to guide incident light into a photospectometer. Other detector schemes are possible.

As shown in FIG. 2, according to one embodiment of the invention, $NO_x$ detector 12a is operative to determine the amount of nitrous oxide in exhaust plume 7 by measuring the absorption of beam 5 at a wavelength corresponding to known absorption characteristics of $NO_x$. This detector may, for example, take the form of a photo-multiplier tube, photo-diode detector, a photospectrometer utilizing charge coupled devices, or another suitable radiation detector. Preferably, a detector with sensitivity to radiation in the 220–230 nm wavelength range may be used to detect $NO_x$. Such an $NO_x$ detector may also operate in conjunction an optical UV bandpass filter, not shown.

The other detectors 12b–12n may also include a HC detector, a CO detector, a $CO_2$ detector, and a reference detector. Other detectors operable to measure various emission components of an exhaust plume may also be included. These detectors are preferably chosen with the capability to detect radiation in the appropriate range for each exhaust constituent.

Other embodiments and uses of the invention will be apparent to those skilled in the art from consideration of the specification and practice of the invention disclosed herein. The specification and examples should be considered exemplary only. The scope of the invention is to be determined from the claims appended hereto.

What is claimed is:

1. A system for remotely detecting emissions, the system comprising:
    a radiation source, for generating a combined beam of ultraviolet and infrared radiation that propagates along a predetermined path;
    a detector module, for receiving the beam of radiation and measuring at least one parameter, indicative of the relative concentration of at least one emission constituent;
    the detector module further comprising:
        at least one detector to produce an output proportional to at least one characteristic of the received beam;
        at least one beam director that directs the beam to the at least one detector without splitting the beam.

2. The system of claim 1, wherein the at least one beam director comprises a rotating mirror.

3. The system of claim 1, wherein the at least one emission constituent comprises nitrous oxides.

4. The system of claim 1, wherein the at least one beam director comprises a rotating mirror and the at least one detector comprises a real time photospectrometer.

5. A method for remotely detecting emissions, the method comprising:
    generating a combined beam of ultraviolet and infrared radiation that propagates along a predetermined path, wherein the predetermined path is chosen to intersect at least a portion of an emission plume;
    receiving the beam at a detector module;
    directing the beam to at least one radiation detector without splitting the beam; and
    measuring at least one parameter indicative of the relative concentration of at least one emission plume constituent.

6. The method of claim 5, wherein the step of directing the beam includes using a rotating mirror to direct the beam without splitting.

7. The method of claim 5, wherein step of directing the beam includes directing the beam to at least one detector that comprises a real time photospectrometer.

* * * * *